(12) United States Patent
Terashima et al.

(10) Patent No.: US 7,276,145 B2
(45) Date of Patent: Oct. 2, 2007

(54) PH ELECTRODE

(75) Inventors: Masaaki Terashima, Asaka (JP); Osamu Seshimoto, Asaka (JP)

(73) Assignee: FUJIFILM Corporation, Tokyo (JP)

( * ) Notice: Subject to any disclaimer, the term of this patent is extended or adjusted under 35 U.S.C. 154(b) by 779 days.

(21) Appl. No.: 10/621,400

(22) Filed: Jul. 18, 2003

(65) Prior Publication Data
US 2004/0074786 A1 Apr. 22, 2004

(30) Foreign Application Priority Data
Jul. 19, 2002 (JP) .............................. 2002-210804

(51) Int. Cl.
*G01N 27/333* (2006.01)

(52) U.S. Cl. .................. 205/787.5; 205/789; 204/433; 204/418

(58) Field of Classification Search ................ 204/400, 204/416–419, 433; 205/775, 787.5, 789, 205/789.5, 792
See application file for complete search history.

(56) References Cited

U.S. PATENT DOCUMENTS

| 4,282,079 A | * | 8/1981 | Chang et al. ............... 204/420 |
| 4,555,274 A | | 11/1985 | Kitajima et al. ............ 148/240 |
| 4,683,048 A | * | 7/1987 | Yamada et al. ............. 204/416 |
| 4,707,243 A | | 11/1987 | Seshimoto et al. ......... 204/418 |
| 4,789,435 A | | 12/1988 | Seshimoto et al. ......... 205/789 |
| 4,842,712 A | | 6/1989 | Seshimoto et al. .... 204/403.01 |
| H949 H | * | 8/1991 | Ishizuka et al. ............ 204/416 |

FOREIGN PATENT DOCUMENTS

| EP | 0074198 A1 | * | 3/1983 |
| JP | 3-54788 B2 | | 8/1991 |
| JP | 4-50530 B2 | | 8/1992 |
| JP | 4-76577 B2 | | 12/1992 |
| JP | 5-56819 B2 | | 8/1993 |

* cited by examiner

*Primary Examiner*—Alex Noguerola
(74) *Attorney, Agent, or Firm*—Birch, Stewart, Kolasch & Birch, LLP

(57) ABSTRACT

An object of the present invention is to suppress an electric potential drift as described above and improve pH measurement precision in order to obtain practical measurement precision in the dry-type multilayered film-type pH electrode. The present invention provides a complex pH electrode which has at least two ion-selective electrodes comprising a non-conductive support, a pair of electrode layers, an electrolytic layer and an ion-selective membrane where at least one of the ion-selective electrode is a hydrogen ion-selective electrode, wherein the hydrogen ion-selective membrane is saturated with carbon dioxide gas.

13 Claims, 3 Drawing Sheets

PH ELECTRODE

This nonprovisional application claims priority under 35 U.S.C. § 119(a) on patent application Ser. No(s). 210804/2002 filed in JAPAN on Jul. 19, 2002, which is (are) herein incorporated by reference.

TECHNICAL FIELD

The present invention relates to a dry-type pH electrode for measuring a hydrogen ion concentration. The invention particularly relates to a pH electrode for measuring potentiometrically hydrogen ion concentration in a body fluid such as blood or serum, and a method for measuring pH using the same.

BACKGROUND ART

There is a known method for measuring the concentration (or activity) of a specific ion contained in a liquid (tap water, river water, sewage, industrial waste, water, etc.) and a biological body fluid (blood, urine, saliva, etc.) using an ion-selective electrode.

The methods for such measurement include wet-type method and dry-type method. Generally in the wet-type method, a barrel-type electrode having a reference liquid inside the electrode is used. However, this type of electrode is difficult in handling in maintenance, washing, conditioning, life, break and the like of the electrode, and has a defect that some hundred or more microliter of a sample liquid is required in order to dip an electrode in the sample liquid.

In order to eliminate such inconveniences, a method of using a dry-type, film-shaped, ion-selective electrode has been proposed. The dry-type ion-selective electrode is a measuring tool (also referred to as a tool for measuring ion activity) for potentiometrically measuring the concentration of a specific ion contained in a drop amount of an aqueous liquid, particularly a biological body fluid such as blood, urine and saliva. Its basic constitution has been described in Japanese Examined Patent Application Nos. 1991-54788 and 1992-50530 and the like. The ion-selective electrode is a dry-type electrode film having a basic constitution which comprises a support, a conductive metal layer (e.g., silver layer), a layer containing a water-insoluble salt of the metal (e.g., silver chloride layer), an electrolytic layer containing an electrolytic salt (e.g., potassium chloride and sodium chloride) which has the same anion as that of the water-insoluble salt and a cation (e.g. potassium ion and sodium ion) and a binder; and an ion-selective membrane, which are integrally laminated in this order. Two of the electrode films are made in a pair, connected with a bridging member, and connected to a potentiometer and then, the sample liquid (test liquid) and a standard liquid (reference liquid) are spotted on each electrode film, and an electric potential is measured. Thus, the concentration of a specific ion in the sample liquid can be determined. According to the dry-type method using the film-shaped ion-selective electrode, no maintenance is needed for the electrode, the measuring tool can be miniaturized and thus, the ion concentration can be measured on bedside and the amount of the sample liquid necessary for measurement can be largely reduced.

By changing the type of the ion-selective membrane of the dry-type ion-selective electrode, the concentration of inorganic ions such as hydrogen ion ($H^+$), lithium ion ($Li^+$), sodium ion ($Na^+$), potassium ion ($K^+$) magnesium ion ($Mg^{2+}$) calcium ion ($Ca^{2+}$), chlorine ion ($Cl^-$), bicarbonate ion ($HCO_3^-$) or carbonate ion ($CO_3^{2-}$), can be measured.

On the other hand, a complex ion-selective electrode has also been known wherein the ion concentrations of a plurality of ion species can be simultaneously measured by incorporating a plurality of ion-selective electrodes in a measuring tool and supplying a test liquid and a reference liquid once respectively. For example, such electrode is described in Japanese Examined Patent Application Nos. 1992-7657.7 and 1993-56819.

It is clinically important to measure concentrations of the above described inorganic ions in the biological body fluid. Among these inorganic ions, measurement of the concentration of ionized calcium (iCa) in blood is indispensable for diagnosis of calcium metabolic anomaly (e.g., accessory thyroid gland dysfunction, and bone metastasis of a cancer). It is an important measurement item in the monitoring of calcium supply in blood transfusion during a surgical operation (calcium ions may bind to citric acid which is added as an anticoagulant, and blood calcium ion may be reduced) and in the clinical examination screening. On the other hand, the hydrogen ion concentration (pH) is an index for knowing acid-base equilibrium of the body fluid and therefore is an important measurement item. Generally in such clinical examinations, an ionized calcium concentration in blood has been normalized for the concentration at pH 7.4. However, for the normalization, the calcium ion concentration as well as the hydrogen ion concentration must be measured together with.

The dry-type ion-selective electrode is a microchip constituted basically of simple structure as described above, and requires a very small amount of the sample liquid. Therefore, it is very useful in the case where the amount of the sample liquid is limited such as the body fluid. In addition, there are such advantages that the ion-selective electrode having such simple and micro structure can be handled independently from the potentiometer and can be replaced by a new electrode in every measurement.

So far, as ion-selective electrodes of dry-type and multilayered film-type, Na, K and Cl electrodes have already been marketed. The concentration of target ions for measurement in the reference liquid has been adjusted to be within an almost normal range in blood. A principle of measurement based on differential method is mentioned below. As represented by the following formula, one electrode of the pair of left and right electrodes is spotted with the standard liquid (reference liquid) having a known concentration, and the other electrode is spotted with the sample liquid, and differential electric potential occurred in both the electrodes is measured, and the concentration of the specific ion in the sample liquid is determined.

$$E_{ref} = E_0 + (N/z) \cdot \mathrm{Log}(A_{ref})$$

$$E_{sample} = E_0 + (N/z) \cdot \mathrm{Log}(A_{sample})$$

$$E = E_{sample} - E_{ref} = (N/z) \cdot \mathrm{Log}(A_{sample}/A_{ref})$$

wherein,
E: differential electric potential
$A_{ref}$: ion activity in reference liquid
$E_{ref}$: electric potential of reference electrode
$A_{sample}$: ion activity in sample liquid
$E_{sample}$: electric potential of sample electrode
N: Nernst coefficient
$E_0$: electric potential of standard electrode
z: ionic valence.

In the method based on this measuring principle, when a composition of the reference liquid is set to be similar to the concentration of target ions contained in the sample liquid, the electric potential occurred is small, which is preferable for electric potential measurement. Moreover, so-called junction potential occurring at a liquid junction is suppressed to enable measurement with good precision. Following this, the composition of the reference liquid of the pH electrode is set, to be a normal pH range in blood.

However, even by using the reference liquid prepared as described above, there remains such a problem that the electric potential shift (drift) is large in accordance with time period passed after start of measurement. When this drift phenomenon differs between electrodes, measured values may vary and a practical problem arises. Further, this phenomenon reduces in time sequence after production of the electrode. In other words, the electrode immediately after production differs from the electrode in a certain period after production in an electric potential response, and therefore a measurement using a specific calibration curve can not be carried out. Consequently, calibration operation must be carried out for every measurement occasion, but it is comlicated.

DISCLOSURE OF THE INVENTION

Accordingly, an object of the invention is to suppress an electric potential drift as described above and improve pH measurement precision in order to obtain practical measurement precision in the dry-type multilayered film-type pH electrode, and also to provide a means wherein a stable electric potential is obtained immediately after production and a measurement can be carried out on the basis of a single calibration curve.

The present inventors have intensively studied to solve the object as described above. As a result, they have found that the presence or absence of bicarbonate ions among the electrolytic components in blood is involved in the drift of the electric potential of the pH electrode. It is presumed that bicarbonate ions in a sample liquid diffuse in the ion-selective membrane as $CO_2$ after spotting and influence the electric potential of the pH electrode. It is also presumed that carbon dioxide in air is gradually absorbed by the ion-selective membrane of the pH electrode in accordance with time passed and has an effect similar to the effect of diffusion of bicarbonate ions in the sample as $CO_2$ into the ion-selective membrane. In the case where the concentrations of bicarbonate ions contained in the reference liquid and the sample liquid differ from each other, the difference occurs between the response electric potentials of the left and right electrodes. As the result, the drift phenomenon is observed. In the case where the electrode absorbs carbon dioxide in a time course, equal absorption occurs in the left electrode and the right electrode and hence, even if concentrations of bicarbonate ions contained in the reference liquid and the sample liquid differ from each other, no difference in response electric potentials occurs between the left and right electrodes and as the result, the drift is relieved. As described above, bicarbonate ions contained also in the reference liquid in an almost equal concentration. e.g., about 20 mM) to that of the sample liquid (e.g., blood) allowed the drift to be suppressed through cancellation of the diffusion effect of $CO_2$ in the reference liquid side by the test liquid side. Further, by placing the pH electrode immediately after production in an atmosphere of carbon dioxide, the drift could be eliminated at the initial stage. Moreover, combination of the both allowed more stabilizing the pH electrode. The invention was completed on the basis of these findings.

According to the present invention, there is provided a complex pH electrode which has at least two ion-selective electrodes comprising a non-conductive support, a pair of electrode layers constituted of a silver layer and a silver halide layer and electrically insulated from each other, an electrolytic layer and an ion-selective membrane, which are laminated in this order, wherein at least one of the ion-selective electrode is a hydrogen ion-selective electrode, and which is provided with a non-conductive member having an aperture for supplying a test liquid and an aperture for supplying a reference liquid, a first delivering member for delivering said supplied test liquid to one of said ion-selective electrodes, a second delivering member for delivering said supplied reference liquid to the other of said ion-selective electrodes and a bridging member for electrically connecting said test liquid and said reference liquid:

wherein the hydrogen ion-selective membrane is saturated with carbon dioxide gas.

In the complex pH electrode according to the present invention, the hydrogen ion-selective membrane is preferably a membrane composed of tri-n-dodecyl amine (TDDA), trisethylhexyl trimellitate, potassium tetrakis (p-chlorophenyl borate) and vinyl chloride-vinyl acetate copolymer.

According to another aspect of the present invention, there is provided a method for measuring pH of a test liquid, which comprises steps of:

supplying the test liquid and a reference liquid to the complex pH electrode according to claim 1 or 2, and measuring an electric potential difference between electrodes.

Preferably, the reference liquid contains bicarbonate ions having the concentration substantially equal to that of the test liquid. In the case where human whole blood, blood plasma or blood serum is used as a test liquid, the concentration of bicarbonate ions in the reference liquid is preferably 20 to 40 mM.

According to still another aspect of the present invention, there is provided a kit of a complex pH electrode which comprises; a complex pH electrode which has at least two ion-selective electrodes comprising a non-conductive support, a pair of electrode layers constituted of a silver layer and a silver halide layer and electrically insulated from each other, an electrolytic layer and an ion-selective layer, which are laminated in this order, wherein at least one of the ion-selective electrode is a hydrogen ion-selective electrode, and which is provided with a non-conductive member having an aperture for supplying a test liquid and an aperture for supplying a reference liquid, a first delivering member for delivering said supplied test liquid to; one of said ion-selective electrodes, a second delivering member for delivering said supplied reference liquid to the other of said ion-selective electrodes and a bridging member for electrically connecting said test liquid and said reference liquid; and a reference liquid containing bicarbonate ions having the concentration substantially equal to that of the test liquid.

In the complex pH electrode kit according to the present invention, the hydrogen ion-selective membrane of the complex pH electrode is preferably saturated with carbon dioxide gas. Preferably, the concentration of bicarbonate ions in the reference liquid is 20 to 40 mM.

According to still another aspect of the present invention, there is provided a method for measuring pH of a test liquid which comprises steps of:

supplying the test liquid and a reference liquid to the complex pH electrode by using the complex pH electrode kit according to any of claims 6 to 8; and measuring the electric potential difference between electrodes.

According to still another aspect of the present invention, there is provided a pH electrode for analyzing a hydrogen ion, which comprises a non-conductive support, a pair of electrode layers constituted of a silver layer and a silver halide layer and electrically insulated from each other, an electrolytic layer and an hydrogen ion-selective membrane, which are laminated in this order, and which is provided thereon with a first non-conductive member having an aperture for supplying a test liquid in correspondence with one of said electrode layers, a second non-conductive member having an aperture for supplying a reference liquid in correspondence with the other of said electrode layers and a bridging member for electrically connecting said test liquid and said reference liquid at apertures:

wherein the hydrogen ion-selective membrane is saturated with carbon dioxide gas.

In the pH electrode according to the present invention, the hydrogen ion-selective membrane is preferably a membrane composed of tri-n-dodecyl amine (TDDA), trisethylhexyl trimellitate, potassium tetrakis (p-chlorophenyl borate) and vinyl chloride-vinyl acetate copolymer.

According to still another aspect of the present invention, there is provided a method for measuring pH of a test liquid, which comprises steps of:

supplying the test liquid and a reference liquid to the pH electrode according to claim 10 or 11; and measuring the electric potential difference between electrodes.

Preferably, the reference liquid contains bicarbonate ions having the concentration substantially equal to that of the test liquid. More preferably, the concentration of bicarbonate ions in the reference liquid is 20 to 40 mM.

DETAILED DESCRIPTION OF THE INVENTION

Figure 1:
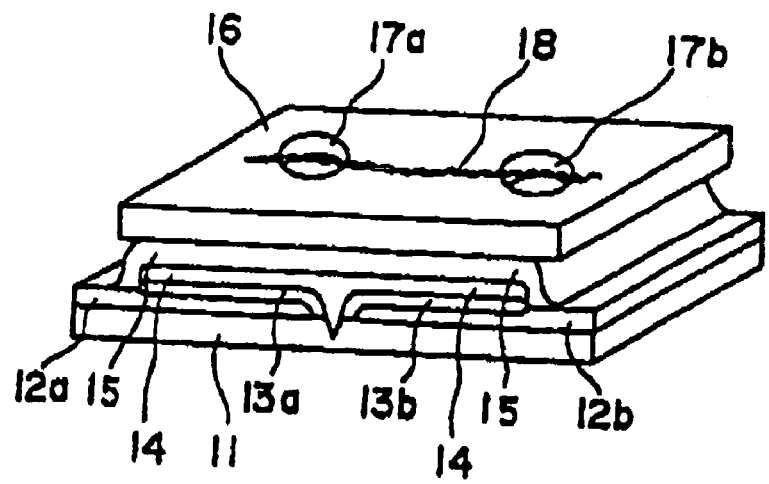
FIG. 1 is a schematic perspective view showing an example of a constitution of the ion selective electrode for analysis of calcium ions or hydrogen ions according to the present invention.
Figure 2:
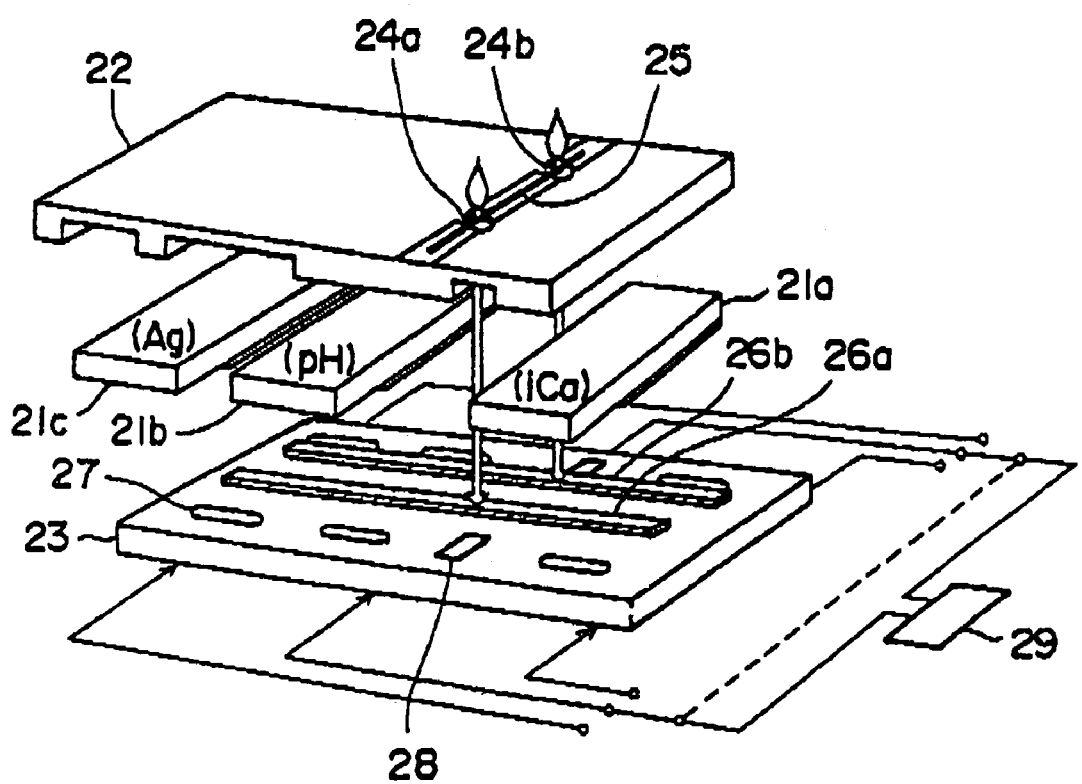
FIG. 2 is an exploded perspective view showing an example of a constitution of the complex pH electrode according to the present invention.

The pH electrode according to the invention can take various constitutions. Some examples will be described with reference to drawings, FIG. 1 is a schematic perspective view showing an example of constitution of the pH electrode for analysis of calcium ions or hydrogen ions according to the invention. In FIG. 1, the pH electrode has a constitution comprising a non-conductive support 11, silver layers 12a and 12b (the silver layers, as illustrated, are separated into two regions by a cut groove reaching a portion of a surface of the support), silver chloride layers 13a and 13b, an electrolytic layer 14, and a hydrogen ion-selective membrane 15, which are laminated in this order, On the hydrogen ion-selective membrane 15 is mounted a water-impermeable non-conductive member 16, on which are provided an aperture 17a for supplying the test liquid and an aperture 17b for supplying the reference liquid in positions corresponding to each of the pair of silver and silver chloride layers (electrode layer). On apertures 17a and 17b is installed a bridging member 18 for connecting electrically the test liquid and the reference liquid, FIG. 2 is an exploded perspective view showing an example of constitution of the complex pH electrode according to the invention. In the complex pH electrode of FIG. 2 are disposed three pairs of film-shaped ion-selective electrodes 21a, 21b and 21c between an upper frame 22 and a lower frame 23. On the upper frame 22 are formed an aperture 24a for supplying the test liquid and an aperture 24b for supplying the reference liquid. On apertures 24a and 24b is installed a bridging member 25 for connecting electrically the test liquid and the reference liquid. On a top face of lower frame 23 are installed delivering members 26a and 26b for delivering horizontally each the test liquid and the reference liquid to each electrode. On the lower frame 23 are formed holes 27 for exposing downwardly electrode connection areas of both ends of each ion-selective electrode, and air vent holes 28. Any of three pairs of film-shaped ion-selective electrodes 21a, 21b and 21c has the layer structure same as that of FIG. 1 described above, and is disposed in an inverted state so as to position the ion-selective membrane in a bottom side.

In FIG. 2, 21a among three pairs of ion-selective electrodes is a calcium ion-selective electrode pair, 21b is a hydrogen ion-selective electrode pair, and 21c is a dummy electrode pair made mainly of metal silver, which plays a discharge function. In the complex pH electrode according to the present invention, the ion-selective electrode is not limited to three pairs, but as long as two of a plurality of electrode pairs are the calcium ion-selective electrode and the hydrogen ion-selective electrode, rest of the electrode pairs can be an electrode pair having any ion selectivity or a dummy electrode pair which plays a discharge function.

In FIGS. 1 and 2 as mentioned above, a case is explained wherein one of the ion-selective electrodes is a calcium ion-selective electrode and the other is a hydrogen ion-selective electrode. In the present invention, it is sufficient that at least one of ion-selective electrodes is a hydrogen ion-selective electrode. As other ion-selective electrodes, ion-selective electrodes other than the calcium ion-selective electrode can be used.

In the complex pH electrode according to the present invention, a thickness of ion-selective membrane other than the hydrogen ion-selective membrane is not particularly limited. However, in order to increase precision of measurement, particularly reproducibility of measured value, the membrane thickness is preferably from 5 µm to 30 µm, more preferably from 5 µm to 20 µm, and particularly preferably from 10 µm to 18 µm.

A material of the calcium ion-selective membrane can be selected and used from materials which are publicly known as a calcium ion-selective membrane of the ion-selective electrode, as describe below. Particularly preferred materials are a combination of calcium di[4-(1,1,1,3-tetramethylbutyl) phenyl] phosphate, dioctylphenyl phosphate (plasticizer) and vinyl chloride-vinyl acetate copolymer. These materials and the publicly known materials can be used in appropriate combination.

On the other hand, as the ion-selective membrane of the hydrogen ion-selective electrode, in order to prevent time-sequential deterioration of the function of the electrode and increase precision of the measurement, particularly reproducibility of measured value, tri-n-dodecylamine and tris-ethylhexyl trimellitate are used as a plasticizer. The particularly preferable combination of the ion-selective membrane is a combination of tri-n-dodecylamine, trisethylhexyl trimellitate, potassium tetrakis (p-chlorophenyl borate) and vinyl chloride-vinyl acetate copolymer. These materials and other publicly known materials can be used in appropriate combination.

The thickness of the hydrogen ion-selective membrane is not particularly limited, but in order to increase reproducibility of measured values and keep a balance of the left and right electrodes of the electrode pair, which is an inherent problem of differential potentiometry, the thickness is preferably from 5 μm to 30 μm, and more preferably from 5 μm to 20 μm.

Any of ion-selective membranes as described above can be formed by means of conventionally known methods. For example, the material composed of the aforementioned combination is dissolved in an appropriate solvent and then, coated onto the electrolytic layer and dried to finish. At this time, for stabilizing a performance of the electrode, 24-hour aging is preferably conducted at a temperature of 35° C.

According to a first aspect of the invention, a hydrogen ion-selective membrane saturated with carbon dioxide gas is used. In order to saturate the hydrogen ion-selective membrane with carbon dioxide gas, the hydrogen ion-selective membrane itself may be independently treated with carbon dioxide gas (e.g., dry ice), or the pH electrode into which a hydrogen ion-selective membrane was incorporated may be treated with carbon dioxide gas.

The method for $CO_2$ treatment for saturating the hydrogen ion-selective membrane with carbon dioxide gas is not particularly limited. For example, it may be carried out by placing the hydrogen ion-selective membrane or the pH electrode comprising the membrane in an appropriate container such as a box or bag (preferably a sealable box or bag) containing an appropriate amount of dry ice. A period for dry ice treatment is not particularly limited. Treatment for several hours to several enables the hydrogen ion-selective membrane to be saturated with carbon dioxide gas. Alternatively, without use of the container, carbon dioxide gas may be directly blown to the hydrogen ion-selective membrane or the pH electrode containing the same.

By using such a hydrogen ion-selective membrane saturated with carbon dioxide gas, the electric potential drift can be suppressed.

According to a second aspect of the present invention, a reference liquid containing bicarbonate ions at a substantially equal concentration to that of a test liquid is used. In the case where the test liquid is blood (whole blood), the concentration of bicarbonate ions contained in the reference liquid is particularly preferably 20 to 40 mM. By using such reference liquid containing bicarbonate ions, the electric potential drift can be suppressed.

In the reference liquid used in the present invention, pH measurement of not only blood but also other liquids can be carried out by properly adjusting the ion concentration. By using the pH electrode according to the present invention, the pH of body fluid other than blood, food, industrial waste water, soil or the like, can be measured.

The present invention can provide the reference liquid containing bicarbonate ions at a concentration substantially equal to that of a test liquid as described above, in a form of a kit in combination of the pH electrode. The pH electrode contained in the kit according to the invention is a complex pH electrode which has at least two ion-selective electrodes comprising a non-conductive support, a pair of electrode layers, constituted of a silver layer and a silver halide layer and insulated electrically from each other, an electrolytic layer, and an ion-selective membrane, which are laminated in this order, wherein at least one of the two ion-selective electrodes is a hydrogen ion-selective electrode, and which is provided with a non-conductive member having an aperture for supplying a test liquid and an aperture for supplying a reference liquid, a first delivering member for delivering a supplied test liquid to one electrode of individual ion-selective electrodes, a second delivering member for delivering a supplied reference liquid to the other electrode, and a bridging member for connecting electrically the test liquid and the reference liquid.

In a particularly preferable aspect of the kit according to the invention, the complex pH electrode in which the hydrogen ion-selective membrane is saturated with carbon dioxide gas, can be used.

In the present invention the pH electrode is not limited to the constitutions of the above described FIGS. 1 and 2, but can take various publicly known constitutions. In addition, a materials of individual layers and individual members of the pH electrode and a method of manufacture thereof can be selected from publicly known materials and methods, and can be used. Such constitutions, materials and methods of the pH electrode have been described in detail in, for example, each publication of Japanese Examined Patent Application No. 1983-4981, Japanese Kokai Nos. 1977-142584, 1982-17852 and 1983-211648, Japanese Examined Patent Application No. 1992-50530; each U.S. Pat. Nos. 4,053,381, 4,171,246 and 4,214,968; a paper no. 16113 (1977 September issue) published on a journal "Research Disclosure".

Measurement of the blood pH and the concentration of calcium ion in blood can be conducted using the complex pH electrode according to the present invention as follows. For example, on apertures 24a and 24b of the complex pH electrode as shown in FIG. 2, blood which is a test liquid and a reference liquid are supplied by spotting, respectively. The test liquid and the reference liquid which were supplied, penetrate into the delivering members 26a and 26b respectively as indicated with an arrow head in FIG. 2. They are sent by the delivering members, and are supplied to the surface of the ion-selective membrane of individual ion-selective electrodes 21a, 21b and 21c so as to cause finally the difference in electric potentials between the electrode pairs of individual ion-selective electrodes. This difference in electric potentials is measured by a potentiometer 29 respectively through the electric connection areas of both ends of each electrode.

The calcium ion concentration and the hydrogen ion concentration are calculated from measured value obtained and a predetermined calibration curve, and then the concentrations are assigned to the formula: Log (iCa at 7.4)=Log (iCa at pH) −0.22×(7.4-pH) (wherein iCA represents calcium ion concentration and pH represents hydrogen ion concentration) and converted to detect a normalized calcium ion concentration at pH 7.4. In this way, once measurement enables obtaining both concentrations of calcium ion and hydrogen ion and also enables obtaining accurately and readily the normalized concentration of calcium ion at pH 7.4, which is ordinarily required for a clinical examination.

The pH electrode according to the invention is not limited to measurement of the calcium ion concentration and/or the hydrogen ion concentration in blood as described above. By changing the concentration of the reference liquid, the pH electrode can be applied to the sample having a higher concentration or lower concentration than that of the reference liquid (e.g., food and the body fluid other than blood). Moreover, when the sample is rain water, tap water and the like, hardness, acidity and basicity of water can also be measured.

EXAMPLES

Example 1

Calcium Ion-Selective Electrode

A metal silver layer (deposited silver layer) with a thickness of about 800 nm was formed on a polyethylene terephthalate film (support, thickness: 188 μm, size; 30 mm×100 mm) by vacuum evaporation. Both ends of this silver layer were covered and protected with a polymer composition liquid resist which was disclosed in Japanese Kokai No. 1983-102146. On the other hand, a central portion of the silver layer was cut and removed by using a cutting tool to make an insulating portion having a shallow U-shaped groove.

Subsequently, an uncovered portion of the silver layer was subjected to contact oxidation and chlorination treatment for about 60 seconds by using hydrochloric acid and potassium dichromic acid-containing treatment liquid (an aqueous solution containing 36 mM/L hydrochloric acid and 16 μM/L potassium dichromic acid). After completion of the treatment, a laminated body was washed with water and dried, resulting in obtaining a pair of film-like silver-silver chloride electrode (laminated body composed of the support, silver layer and silver chloride layer).

28.8 g of sodium chloride was dissolved in a mixture solvent of 192 g of ethanol and 240 g of purified water to prepare an electrolytic coating solution. This coating solution was coated onto the silver-silver chloride electrode film and then, the film was left standing in air to dry naturally the coated layer. A weight of the coated layer (electrolytic layer) after drying was 2.1 g/m².

On this electrolytic layer was formed a calcium ion-selective membrane having the following composition to make a film thickness of 26 μm by an ordinary method, so as to obtain the calcium ion-selective electrode. In this procedure, 24 hour aging was conducted at the temperature of 35° C.

[Composition of the Calcium Ion-Selective Membrane]

| Calcium di[4-(1,1,1,3-tetramethylbutyl) phenyl]phosphate (t-HDOPP) | 0.3 g |
|---|---|
| Dioctylphenyl phosphate (DOPP) | 3.0 g |
| Vinyl chloride-vinyl acetate copolymer (VYNS) | 3.0 g |
| Methylethyl ketone | 20 g |

On the ion-selective membrane of the obtained calcium ion-selective electrode was adhesively mounted a liquid receiving mask, which is made of a plastic film and has two liquid receiving holes. Then, a polyester spun yarn-made bridge was installed to connect the liquid receiving holes. Thus, many numbers of ion-selective electrodes for analysis of calcium ion according to the present invention were manufactured (see FIG. 1).

Example 2

Hydrogen Ion-Selective Electrode

A metal silver layer (deposited silver layer) with a thickness of about 800 nm was formed on a polyethylene terephthalate film (support, thickness: 188 μm, size: 30 mm×100 mm) by vacuum evaporation. Both ends of this silver layer were covered and protected with a polymer composition liquid resist which was disclosed in Japanese Kokai No. 1983-102146. On the other hand, a central portion of the silver layer was cut and removed by using a cutting tool to make an insulating portion with a shallow U-shaped groove.

Subsequently, an uncovered portion of the silver layer was subjected to contact oxidation and chlorination treatment for about 60 seconds by using hydrochloric acid and potassium dichromic acid-containing treatment liquid (an aqueous solution containing 36 mM/L hydrochloric acid and 16 mM/L potassium dichromic acid). After completion of the treatment, a laminated body was washed with water and dried to obtain a pair of film-like silver-silver chloride electrode (laminated body composed of the support, silver layer and silver chloride layer).

28.8 g of sodium chloride was dissolved in a mixture solvent of 192 g of ethanol and 240 g of purified water to prepare an electrolytic coating solution. This coating solution was coated onto the silver-silver chloride electrode film and then, the film was left standing in air to dry naturally the coated layer. A weight of the coated layer (electrolytic layer) after drying was 2.1 g/m².

On this electrolytic layer was formed a hydrogen ion-selective membrane having the following composition to make the film thickness in 20 μm by an ordinary method, so as to obtain the hydrogen ion-selective electrode. In this procedure, 24 hour aging was conducted at the temperature of 35° C.

[Composition of the Hydrogen Ion-Selective Membrane]

| Tri-n-dodecylamine (TDDA) | 0.1 g |
|---|---|
| Trisethylhexyl trimellitate (Tris EHT) | 3.0 g |
| Potassium tetrakis (p-chlorophenyl borate) (KTpCPB) | 0.06 g |
| Vinyl chloride-vinyl acetate copolymer (VYNS) | 3.0 g |
| Methylethyl ketone | 20 g |

On the ion-selective membrane of the obtained hydrogen ion-selective electrode was adhesively mounted a liquid receiving mask, which is made of a plastic film and has two liquid receiving holes. Then, a polyester spun yarn-made bridge was installed to connect the liquid receiving holes. Thus, many numbers of ion-selective electrodes for analysis of hydrogen ion according to the present invention were manufactured (see FIG. 1).

Example 3

Complex pH Electrode

The calcium ion-selective electrode obtained in Example 1, the hydrogen ion-selective electrode (pH electrode) obtained in Example 2, and a dummy electrode separately made from the support and metal silver layer were sandwiched, while positioning the support in a top position and the ion-selective membrane and the metal silver layer in a bottom position respectively, with the liquid receiving mask made of a plastic film having two liquid receiving holes, and a delivering mask also made of a plastic film to be adhesively mounted. Then, the polyester spun yarn-made bridge was installed to connect the liquid receiving holes to manufacture the complex pH electrode according to the invention (see FIG. 2).

The complex pH electrode obtained as described above was placed in a box in which dry ice was filled, and was subjected to treatment for 8 hours at an ordinary temperature. As a complex pH electrode for comparison, a complex pH electrode which was not subjected to this dry ice treatment was used.

Example 4

Performance Test of the Complex pH Electrode

Using the complex pH electrode prepared in Example 3, electric potential was measured for five times at 30, 45 and 60 seconds after spotting whole blood, and a reference liquid (composition is presented below) containing $NaHCO_3$ or a reference liquid not containing $NaHCO_3$ (composition is the same as below, excluding lack of $NaHCO_3$), with a potentiometer (FDC800, Fuji Photo Film K.K. made).

(Composition of the First Reference Liquid Containing $NaHCO_3$)

| | |
|---|---|
| Nacl | 100 mM |
| MOPS | 40 mM |
| PVP K-15 | 3.0% |
| glycerin | 2.0% |
| ProClin 150 | 0.05% |
| $NaHCO_3$ | 20 mM |
| $CaCl_2$ | 1.25 mM |
| pH | 7.15 |

Figure 3:
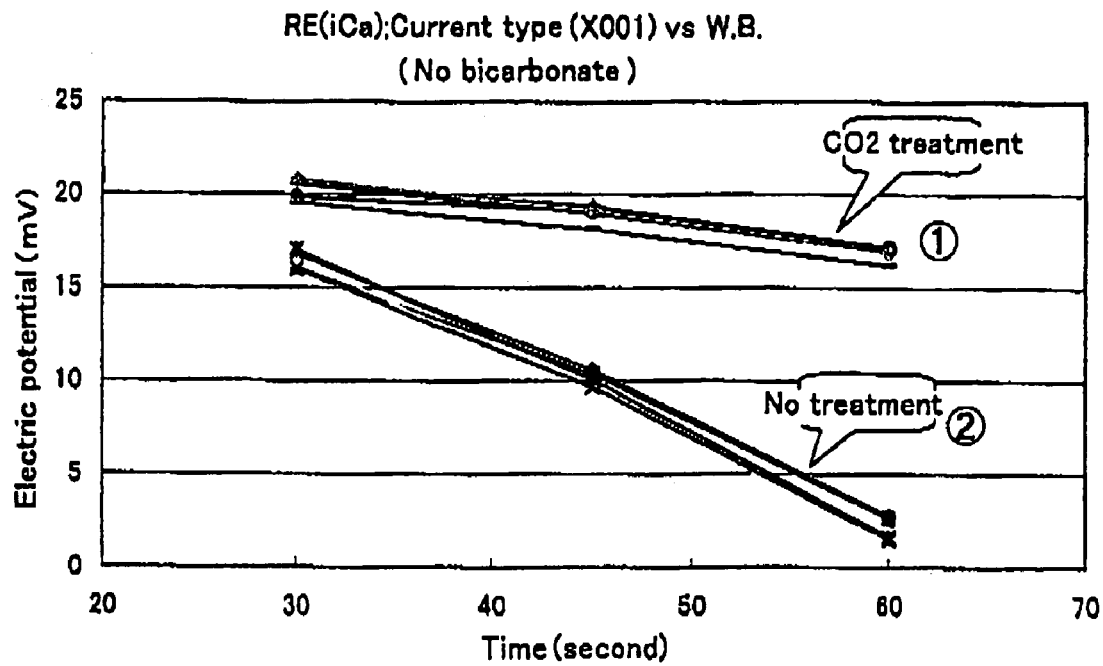
FIG. 3 shows the result of measurement of an electric potential in the case where a reference liquid containing no $NaHCO_3$ was used.
Figure 4:
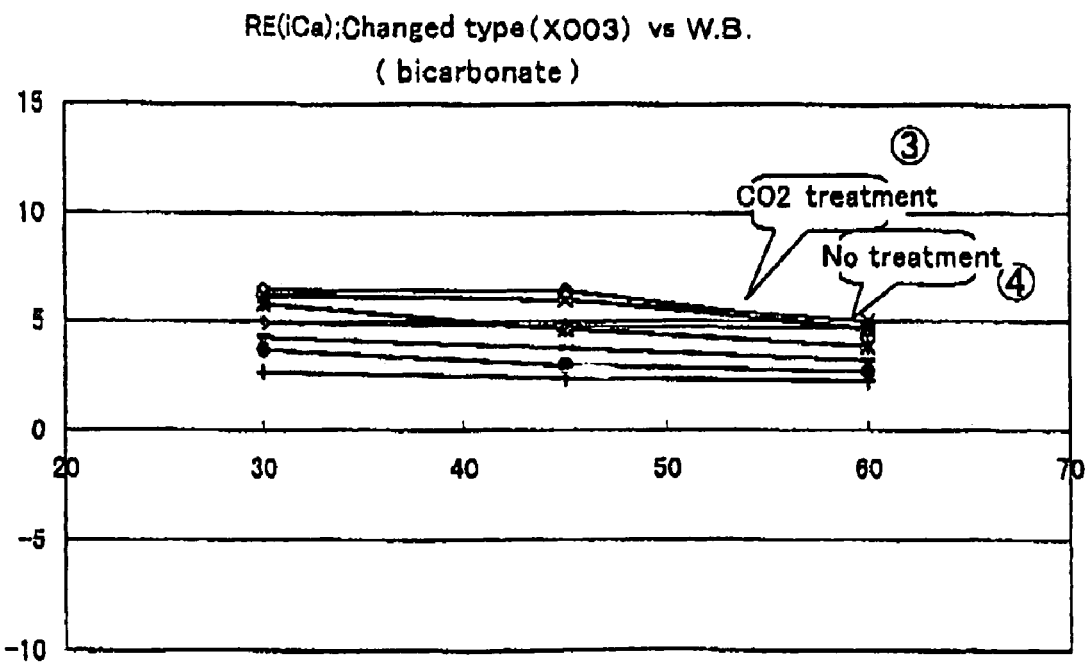
FIG. 4 shows the result of measurement of an electric potential in the case where a reference liquid containing $NaHCO_3$ was used.

The result is shown in FIGS. 3 and 4.

FIG. 3 shows the result of the case where the reference liquid containing no $NaHCO_3$ was used. In the figure, "$CO_2$-treated" shows the result of the case where the complex pH electrode subjected to dry ice treatment was used (result of Example of the invention). "Not treated" shows the result of the case where the complex pH electrode not subjected to dry ice treatment was used (result of Comparative Example).

FIG. 4 shows the result of the case where the reference liquid containing $NaHCO_3$ was used. In the figure, "$CO_2$-treated" shows the result of the case where the complex pH electrode subjected to dry ice treatment was used (result of Example of the invention). "Not treated" shows the result of the case where the complex pH electrode not subjected to dry ice treatment wash used (result of Example of the invention).

As is understood from the results of FIGS. 3 and 4, it has been found that use of the complex pH electrode subjected to dry ice treatment and/or use of the reference liquid containing $NaHCO_3$ enables to suppress the electric potential drift. On the other hand, in the case where the complex pH electrode was not subjected to dry ice treatment and the reference liquid containing no $NaHCO_3$ was used (in FIG. 3, the result where "Not treated" is indicated), a large electric potential drift occurred.

Figure 5:
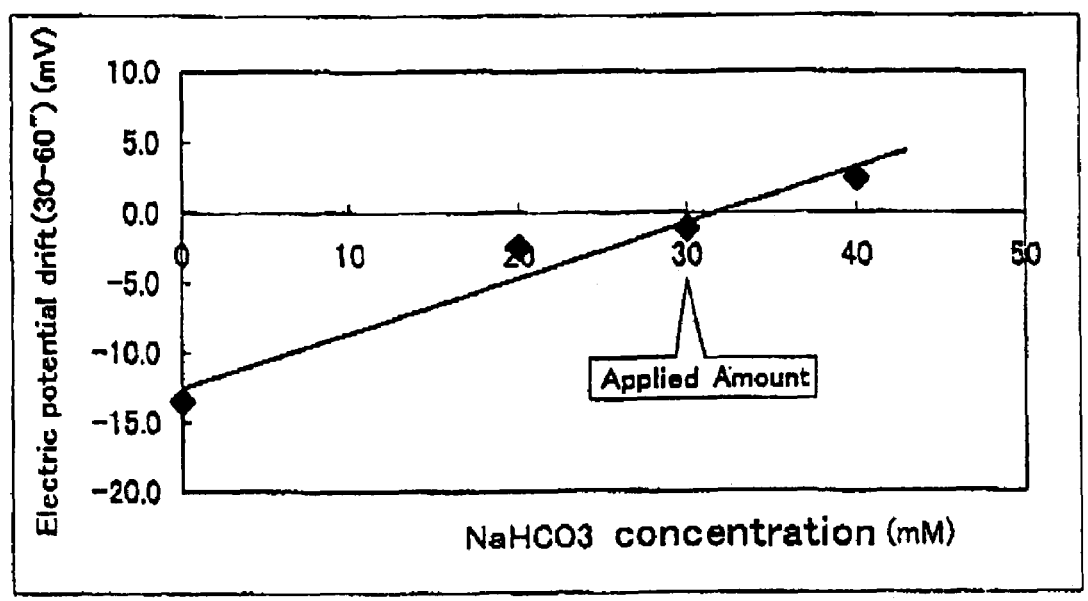
FIG. 5 shows the result of measurement of the electric potential drift at 30 seconds and 60 seconds after spotting, while setting $NaHCO_3$ concentration of the reference liquid to 0, 20, 30 or 40 mM.

In addition, $NaHCO_3$ concentration in the reference liquid was set to 0, 20, 30 or 40 mM and, as described above, the potentiometer (FDC800, Fuji Photo Film K.K. made) was used to measure the electric potential drift at 30 seconds and 60 seconds after spotting. The result is presented in FIG. 5. As is understood from the results of FIG. 5, by setting $NaHCO_3$ concentration of the reference liquid to be 20 to 40 mM, the electric potential drift can be suitably suppressed.

INDUSTRIAL APPLICABILITY

According to the present invention, in order to realize practical measurement precision for the pH electrode of dry-type and multilayered film-type, pH measurement precision can be improved by suppressing the drift as described above. Moreover, according to the pH electrode of the present invention, a stable electric potential can be obtained immediate after manufacture, and measurement can be carried out using a single calibration curve.

What is claimed is:

1. A complex pH electrode which has at least two ion-selective electrodes comprising a non-conductive support, a pair of electrode layers constituted of a silver layer and a silver halide layer and electrically insulated from each other, an electrolytic layer and an ion-selective membrane, which are laminated in this order, wherein at least one of the ion-selective electrode is a hydrogen ion-selective electrode, and which is provided with a non-conductive member having an aperture for supplying a test liquid and an aperture for supplying a reference liquid, a first delivering member for delivering said supplied test liquid to one of said ion-selective electrodes, a second delivering member for delivering said supplied reference liquid to the other of said ion-selective electrodes and a bridging member for electrically connecting said test liquid and said reference liquid:
wherein the hydrogen ion-selective membrane is saturated with carbon dioxide gas.

2. The complex pH electrode according to claim 1, wherein the hydrogen ion-selective membrane is a membrane composed of tri-n-dodecyl amine (TDDA), trisethylhexyl trimellitate, potassium tetrakis (p-chlorophenyl borate) and vinyl chloride-vinyl acetate copolymer.

3. A method for measuring pH of a test liquid, which comprises steps of:
supplying the test liquid and a reference liquid to the complex pH electrode according to claim 1, and
measuring an electric potential difference between electrodes.

4. The method according to claim 3, wherein the reference liquid contains bicarbonate ions having the concentration substantially equal to that of the test liquid.

5. The method according to claim 3, wherein the concentration of bicarbonate ions in the reference liquid is 20 to 40 mM.

6. A kit of a complex pH electrode which comprises;
a complex pH electrode, which has at least two ion-selective electrodes comprising a non-conductive support, a pair of electrode layers constituted of a silver layer and a silver halide layer and electrically insulated from each other, an electrolytic layer and an ion-selective layer, which are laminated in this order, wherein at least one of the ion-selective electrode is a hydrogen ion-selective electrode, and which is provided with a non-conductive member having an aperture for supplying a test liquid and an aperture for supplying a reference liquid, a first delivering member for delivering said supplied test liquid to one of said ion-selective electrodes, a second delivering member for delivering said supplied reference liquid to the other of said ion-selective electrodes and a bridging member for electrically connecting said test liquid and said reference liquid;
a reference liquid containing bicarbonate ions having the concentration substantially equal to that of the test liquid; and
wherein the hydrogen ion-selective membrane of the complex pH electrode is saturated with carbon dioxide gas.

7. The complex pH electrode kit according to claim 6, wherein the concentration of bicarbonate ions in the reference liquid is 20 to 40 mM.

8. A method for measuring pH of a test liquid which comprises steps of:
supplying the test liquid and a reference liquid to the complex pH electrode by using the complex pH electrode kit according to claim 6 or 7; and
measuring the electric potential difference between electrodes.

9. A pH electrode for analyzing a hydrogen ion, which comprises a non-conductive support, a pair of electrode layers constituted of a silver layer and a silver halide layer and electrically insulated from each other, an electrolytic layer and an hydrogen ion-selective membrane, which are laminated in this order, and, which is provided thereon with a first non-conductive member having an aperture for supplying a test liquid in correspondence with one of said electrode layers, a second non-conductive member having an aperture for supplying a reference liquid in correspondence with the other of said electrode layers and a bridging member for electrically connecting said test liquid and said reference liquid at apertures:
wherein the hydrogen ion-selective membrane is saturated with carbon dioxide gas.

10. The pH electrode according to claim 9, wherein the hydrogen ion-selective membrane is a membrane composed of tri-n-dodecyl amine (TDDA), trisethylhexyl trimellitate, potassium tetrakis (p-chlorophenyl borate) and vinyl chloride-vinyl acetate copolymer.

11. A method for measuring pH of a test liquid, which comprises steps of:
supplying the test liquid and a reference liquid to the pH electrode according to claim 9 or 10; and
measuring the electric potential difference between electrodes.

12. The method according to claim 11, wherein the reference liquid contains bicarbonate ions having the concentration substantially equal to that of the test liquid.

13. The method according to claim 11, wherein the concentration of bicarbonate ions in the reference liquid is 20 to 40 mM.

* * * * *